US006908738B2

(12) United States Patent
Gelboin et al.

(10) Patent No.: US 6,908,738 B2
(45) Date of Patent: Jun. 21, 2005

(54) AGENTS THAT BIND TO AND INHIBIT HUMAN CYTOCHROME P450 2C19

(75) Inventors: Harry V. Gelboin, Chevy Chase, MD (US); Kristopher W. Krausz, Columbia, MD (US); Frank J. Gonzalez, Bethesda, MD (US)

(73) Assignee: National Institute of Health, Rockville, MD (US)

( * ) Notice: Subject to any disclaimer, the term of this patent is extended or adjusted under 35 U.S.C. 154(b) by 462 days.

(21) Appl. No.: 09/950,431

(22) Filed: Sep. 10, 2001

(65) Prior Publication Data

US 2002/0115124 A1 Aug. 22, 2002

(51) Int. Cl.$^7$ ............................................. G01N 33/53
(52) U.S. Cl. ..................... 435/7.1; 435/7.8; 435/69.7; 436/15; 436/548; 436/547
(58) Field of Search ......................... 435/7.1, 7.8, 69.7; 436/15, 548, 547

(56) References Cited

U.S. PATENT DOCUMENTS 5,939,530 A    8/1999   Gelboin et al.
6,060,253 A    5/2000   Gelboin et al.

OTHER PUBLICATIONS

Biochemistry 29(37): 8509–8517.*
Trends in Genetics 15(4): 132–133.*
Trends in Genetics 12(10) 425–427.*
Trends in Biotech. 18(1): 34–39.*
Cheng et al., (1984) Detection and purification of cytochromes P–450 in animal tissues with monoclonal antibodies *JBC* 259:12279–12284.
Crespi et al., (1989) Transfection of a human cytochrome P–450 gene into the human lymphoblastoid cell line, AHH–1, and use of the recombinant cell line in gene mutation assays *Carcinogenesis* 10:295–301.
Crespi CL (1995) Xenobiotic Metabolizing Human Cells as Tools for Pharmacological and Toxicological Research. *Adv in Drug Research* 26:180–216.
Crespi,CL and BW Penman (1997) Use of cDNA Expressed Human Cytochrome P450 Enzymes to Study Potential Drug–Drug Interactions. *Adv in Pharmacology* 43:171–188.
Edwards et al., (1998) Development of a Comprehensive Panel of Antibodies Against the Major Xenobiotic Metabolizing Forms of Cytochrome P450 in Humans. *Gene Expression and Development* 56(3):377–387.
Eichelbaum et al., (1992) Genetically determined differences in drug metabolism as a risk factor in drug toxicity. *Toxicology Letters* 64/65:155–122.
Fujino et al., (1982) Phenotyping of Cytochromes P–450 in Human Tissues with Monoclonal Antibodies. *Proc Natl Acad Sci USA* 79:3682–3686.
Gelboin (1993) Cytochrome P450 and Monoclonal Antibodies. *Pharmacol Rev* 45:413–453.

Gelboin et al., (1995) Inhibitory and Non Inhibitory Monoclonal Antibodies to Human Cytochrome P450 3A3/4. *Biochem Pharmacol* 50:1841–1850.
Gelboin et al., (1996) Inhibitory and Noninhibitory Monoclonal Antibodies to Human Cytochrome P450 2E1. *Chem Res Toxicl* 9:1023–1030.
Gelboin et al., (1997) A Monoclonal Antibody Inhibitory to Human P450 2D6: A Paradigm for use in Combinatorial Determination of Individual P450 role in Specific Drug Tissue Metabolism. *Pharmacogenetics* 7:469–477.
Gelboin HV, et al., (1998) Monoclonal Antibodies to Cytochrome P450 in Methods in Molecular Biology: Cytochrome P450 Protocols. (IR Phillips and EA Shephard, eds) pp 227–237, Humana Press Inc., Totowa, New Jersey.
Gelboin et al., (1999) Inhibitory Monoclonal Antibodies to Human Cytochrome P450 Enzymes: A New Avenue for Drug Discovery. *Trends Pharmacol Sci* 20(11):432–438.
Gonzalez et al., (1988) The molecular biology of cytochrome P450s. *Pharmacol. Rev.* 40:243–288.
Gonzalez et al., (1991) Expression of mammalian cytochrome P450 using baculovirus *Meth. Enzymol.* 206:93–99.
Gonzalez and J.Idle, (1994) Pharmacogenetic phenotyping and genotyping. Present status and future potential. *Clin. Pharmacokin.* 26:59–70.
Gonzalez, FJ and KR Korzekwa (1995) Human Cytochromes P450 Expression Systems. *Annu Rev Pharmacol Toxicol* 35:369–390.
Ioannides (1996) Cytochromes P450 Metabolic and Toxicological Aspects. CRC Press, New York.
Krausz et al., (2000) An Inhibitory Monoclonal Antibody to Human Cytochrome P450 that Specifically Binds and Inhibits P4502C9II, an Allelic Variant of P4502C9 Having a Single Amino Acid Change Arg144 Cys. *Xenobiotica* 30:619–625.
Nebert et al., (1991) The P450 superfamily: update on new sequences, gene mapping, and recommended nomenclature *DNA & Cell Biology* 10:1–14.
Nelson et al., (1996) P450 superfamily: update on new sequences, gene mapping, accession numbers and nomenclature *Pharmacogenetics* 6:1–42.
Omura, T. and R. Sato (1964) The Carbon Monoxide–Binding Pigment of Liver Microsomes. I. Evidence for its Hemoprotein Nature. *J Biol Chem* 239:2370–2378.

(Continued)

*Primary Examiner*—Long V. Le
*Assistant Examiner*—Jacob J. Cheu
(74) *Attorney, Agent, or Firm*—Townsend & Townsend & Crew LLP; Nathan S. Cassell

(57) ABSTRACT

The invention provides monoclonal antibodies and other binding agents to human cytochrome P450 2C19 having advantageous properties, including capacity substantially to inhibit enzyme activity of human cytochrome P450 2C19 and lack of specific binding to other human cytochrome P450s. The binding agents of the invention are useful inter alia in methods for screening drugs for metabolism by cytochrome P450 2C19, and in methods of measuring P450 2C19 levels in individuals relative to P450 2C19 levels in a control population.

14 Claims, 3 Drawing Sheets-

OTHER PUBLICATIONS

Park et al., (1982) Monoclonal Antibodies That Inhibit Enzyme Activity of 3–Methycholanthracene–Induced Cytochrome P–450. *Cancer Res* 42:1798–1808.

Park et al., (1989) Monoclonal Antibodies to Rat Liver Cytochrome P–450 2c/RLM5 That Regiospecifically Inhibit Steroid Metabolism. *Biochem Pharmacol* 38(18):3067–3074.

Relling et al., (1990) Tolbutamide and Mephenytoin Hydroxylation by Human Cytochrome P450s in the CYP2C Subfamily. *J Pharmacol Exp Ther* 252:442–447.

Remmel and B Burchell (1995) Validation and Use of Cloned Expressed Human Drug Metabolizing Enzymes in Heterogeneous Cells for Analysis of Drug–Drug Interaction. *Biochem Pharmacol* 46:559–566.

Rendic and FJ DiCarlo (1997) Human Cytochrome P450 Enzymes: A Status Report Summarizing Their Reactions Substrates, Inducers and Inhibitors. *Drug Metab Rev* 29:413–580.

Romkes et al., (1991) Cloning and expression of complementary DNAs for multiple members of the human cytochrome P450IIC subfamily. *Biochemistry* 30:3247–3255.

Schulz–Utermoehl et al., (2000) Selective and Potent Inhibition of Human CYP2C19 Activity by a Conformationally Targeted Antipeptide Antibody. *Drug Metab and Dispos* 28:715–717.

Shimada et al., (1994) Interindividual Variations in Human Liver Cytochrome P450 Enzymes involved in the Oxidation of Drugs, Carcinogens and Toxic Chemicals: Studies with Liver Microsomes of 30 Japanese and 30 Caucasions. *J Pharmacol Exp Ther* 270:414–423.

Shou et al., (1994) Regio– and stereo–selective metabolism of phenanthrene by twelve cDNA–expressed human, rodent, and rabbit cytochromes P–450. *Cancer Lett.* 83(1–2):305–313.

Streetman et al., (2000) Phenotyping of Drug–Metabolizing Enzymes in Adults: A Review of *In Vivo* Cytochrome P450 Phenotyping Probes. *Pharmacogenetics* 10:187–216.

Venkatakrishnan et al., (2000) Comparison Between Cytochrome P450 (CYP) Content and Relative Activity Approaches to Scaling from cDNA Expressed CYPs to Human Liver Microsomes: Ratio of Accessory Proteins as Sources of Discrepancies Between the Approaches. *Drug Metab and Dispos* 28(12):1493–1504.

Wester et al., (2000) CYP 2C19 Participates in Tolbutamide Hydroxylation by Human Liver Microsomes. *Drug Metab Dispos* 28(3):354–359.

Yang et al., (1998a) Inhibitory Monoclonal Antibodies to Human Cytochrome P450 1A2: Analysis of Phenacetin o–Deethylation in Human Liver. *Pharmacogenetics* 8:375–382.

Yang et al., (1998b) Inhibitory Monoclonal Antibody to Human Cytochrome P450 2B6. *Biochem Pharmacol* 55:1633–1640.

Yang et al., (1998c) Role of cDNA Expressed Human Cytochromes P450 in the Metabolism of Diazepam. *Biochem Pharmacol* 55:889–896.

Yang et al., (1999) Eight Inhibitory Monoclonal Antibodies Define the Role of Individual P450s in Human Liver Microsomal Diazepam, 7–Ethoxycoumarin and Imipramine Metabolism. *Drug Metab Dispos* 27:102–109.

* cited by examiner

AGENTS THAT BIND TO AND INHIBIT HUMAN CYTOCHROME P450 2C19

BACKGROUND OF THE INVENTION

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," TO TABLE, OR A COMPUTER PROGRAM LISTING APPENDIX SUBMITTED ON A COMPACT DISK

NOT APPLICABLE

BACKGROUND OF THE INVENTION

The human cytochrome P450s collectively metabolize a multitude of drugs and non-drug xenobiotics including toxins, mutagens and carcinogens as well as endobiotics such as steroids, prostaglandins and fatty acids. Drug metabolism in human liver is primarily catalyzed by twelve major microsomal P450 enzymes having different substrate and product specificities and are heterogeneously distributed in tissues (Ioannides, 1996, CYTOCHROMES P450 METABOLIC AND TOXICOLOGICAL ASPECTS. CRC Press, New York) (Rendic and DeCarlo, 1997, *Drug Metab Rev* 29:413–580). P450-catalyzed metabolism of drugs and non-drug xenobiotics is a key element in drug disposition and may be responsible for certain adverse drug reactions, chemical toxicity and immunotoxicity (Ioannides, 1996, CYTOCHROMES P450 METABOLIC AND TOXICOLOGICAL ASPECTS. CRC Press, New York).

The human cytochrome P450 2C sub-family consists of four isoforms 2C8, 2C9, 2C18 and 2C19. The three major alleles of P450 2C9 are the wild type $2C9_{Arg144}(*1)$, $2C9_{Cys144}(*2)$, $2C9_{Ile \rightarrow Leu359}(*3)$ (Haining et al. 1996, Miners and Birkett, 1998, *Clin Pharmacol* 45:525–538; hereinafter referred to as 2C9*1, 2C9*2 and 2C9*3 respectively). The 2C isoforms are collectively among the most important human enzymes responsible for the metabolism of a wide variety of drugs including taxol (Rahman et al., 1994, *Cancer Res* 54:5543–5546) phenytoin, tolbutamide, S-warfarin, losartan, S-mephenytoin and diazepam (Miners and Burkett, 1998, *Clin Pharmacol* 45:525–538).

Monoclonal antibodies ("MAbs") are reagents (Yelton and Scharff, 1981, *Annu Rev Biochem* 50:657–680) that have proved to be of great value for the precise identification, measurement and functional characterization of each P450 isoform (Gelboin, 1993, *Pharmacol Rev* 45:413–453). The MAbs are derived from potentially immortal hybridomas and are specific and highly inhibitory to the enzyme activity of the target P450 and thus are powerful reagents for "reaction phenotyping" i.e., for measuring the metabolic contribution of each of the multiple P450s to a substrates metabolism (Gelboin, 1993, *Pharmacol Rev* 45:413–453)

MAbs specific to seven individual major human liver (HLM) P450 isoforms were described viz., 1A1, (Fujino et al., 1982, *Proc Natl Acad Sci USA* 79:3682–3686), 1A2 (Yang et al., 1998, *Pharmacogenetics* 8:375–382), 2A6 (Sai et al., 1999, *Pharmacogenetics* 9:229–237), 2B6 (Yang et al., 1998, *Biochem Pharmacol* 55:1633–1640), 2D6 (Gelboin et al., 1997, *Pharmacogenetics* 7:469–477), 2E1 (Gelboin et al., 1996, *Chem Res Toxicl* 9:1023–1030) and 3A4/5 (Gelboin et al., 1995, *Biochem Pharmacol* 50:1841–1850) and to the entire 2C sub-family (Yang et al., 1998, *Biochem Pharmacol* 55:889–896; Park et al., 1989, *Biochem Pharmacol* 38(18):3067–3074). The MAbs measured the contribution of each target P450 to the metabolism of a variety of examined drugs (Yang et al., 1999, *Drug Metab Dispos* 27:102–109; Gelboin et al., 1999, *Trends Pharmacol Sci* 20(11):432–438). Many of the MAbs can also be used to measure the tissue P450 protein content by immunoblot analysis.

Genetic polymorphisms of cytochromes P450 result in phenotypically-distinct subpopulations that differ in their ability to perform biotransformations of particular drugs and other chemical compounds. These phenotypic distinctions have important implications for selection of drugs. For example, a drug that is safe when administered to most humans may cause toxic side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals (Eichelbaum et al., 1992, *Toxicology Letters* 64/65, 155–122). Accordingly, it is important to identify individuals who are deficient in a particular P450 enzyme, so that drugs known or suspected of being metabolized by the enzyme are not used, or used only with special precautions (e.g., reduced dosage, close monitoring) in such individuals. Identification of such individuals may indicate that such individuals be monitored for the onset of cancers.

Existing methods of identifying deficiencies in patients are not entirely satisfactory. Patient metabolic profiles are often assessed with a bioassay after a probe drug administration. Poor metabolizers (PM) exhibit physiologic accumulation of unmodified drug and have a high metabolic ratio of probe drug to metabolite. This bioassay has a number of limitations: Lack of patient cooperation, adverse reactions to probe drugs, and inaccuracy due to coadministration of other pharmacological agents or disease effects. See, e.g., Gonzalez et al., 1994, *Clin. Pharmacokin.* 26, 59–70. Genetic assays by RFLP (restriction fragment length polymorphism), ASO PCR (allele specific oligonucleotide hybridization to PCR products or PCR using mutant/wild-type specific oligo primers), SSCP (single stranded conformation polymorphism) and TGGE/DGGE (temperature or denaturing gradient gel electrophoresis), MDE (mutation detection electrophoresis) are time-consuming, technically demanding and limited in the number of gene mutation sites that can be tested at one time.

A complication in patient drug choice is that most drugs have not been characterized for their metabolism by P450 2C family and other cytochromes P450. Without knowing which cytochrome(s) P450 is/are responsible for metabolizing an individual drug, an assessment cannot be made for the adequacy of a patient's P450 profile. For such drugs, there is a risk of adverse effects if the drugs are administered to poor metabolizers.

Monoclonal antibodies that specifically bind to 2C family members and inhibit its activity, if available, could be used to screen drugs for their metabolism by 2C and/or identify 2C poor metabolizers by simple bioassays, thereby overcoming the problems in prior complicated methods discussed above. However, such monoclonal antibodies represent, at best, a small subset of the total repertoire of antibodies to human cytochrome P450 2C, and have not hitherto been isolated. Although in polyclonal sera, many classes of antibody may contribute to inhibition of enzyme activity of P450 2C family members as a result of multiple antibodies in sera binding to the same molecule of enzyme, only a small percentage of these, if any, can inhibit as a monoclonal. A monoclonal antibody can inhibit only by binding in such a manner that it alone block or otherwise perturb the active site of an enzyme. The existence and representation of monoclonal antibodies with inhibitory properties thus depend on many unpredictable factors. Among them are the size of the active site in an enzyme, whether the active site is immunogenic, and whether there are any sites distal to the active site that can exert inhibition due to stearic effects of antibody binding. The only means of obtaining antibodies with inhibitory properties is to screen large numbers of hybridoma until one either isolates the desired antibody or abandons the task through failure.

Notwithstanding these difficulties, the present invention provides inter alia monoclonal antibodies that specifically bind to human cytochrome P450 2C family members and inhibit their activity.

BRIEF SUMMARY OF THE INVENTION

The invention provides isolated binding agents that compete with a monoclonal antibody selected from the group consisting of MAb 1-7-4-8, MAb 1-5-1-3, and MAb 1-1-11-1 for specific binding to human cytochrome P450 2C19, and that specifically inhibits 2C19-catalyzed metabolism of diazapam and phenanthrene by at least 90%.

Preferred binding agents are monoclonal antibodies. Some binding agents lack specific binding to at least one cytochrome P450 selected from the group consisting of human cytochromes P450 1A1, 2A6, 2B6, 2C8, 2C9*1, 2C9*2, 2C9*3, 2C18, 2D6, 2E1, 3A4, and 3A5. Some binding agents lack specific binding to each of human cytochromes P450 1A1, 2A6, 2B6, 2C8, 2C9*1, 2C9*2, 2C9*3, 2C18, 2D6, 2E1, 3A4, and 3A5. Preferred binding agents are able to specifically inhibit the enzyme activity of human cytochrome P450 2C19 by at least 90%. Some binding agents are binding fragments, such as Fab fragments.

MAb 1-7-4-8, MAb 1-5-1-3, and MAb 1-1-11-1 are exemplified monoclonal antibodies. Some other monoclonal antibodies are analogs of these monoclonal antibodies comprising a light chain variable domain having at least 80% sequence identity with the light chain variable domain of a monoclonal antibody selected from the group consisting of MAb 1-7-4-8, MAb 1-5-1-3, and MAb 1-1-11-1, wherein the percentage identity is determined by aligning amino acids in the light chain variable domains by the Kabat numbering convention and a heavy chain variable domain having at least 80% sequence identity with the heavy chain variable domain of a monoclonal antibody selected from the group, wherein the percentage sequence identity is determined by aligning amino acids in the heavy chain variable domains by the Kabat numbering convention.

The invention further provides cell lines producing monoclonal antibodies as described above. Cells lines can be eucaryotic or procaryotic.

The invention further provides methods of determining whether a cytochrome P450 2C family member metabolizes a compound. Such methods entail contacting the compound with cytochrome P450 2C family member in the presence of varying amounts of the binding agents above. Metabolism of the compound is then assayed as a function of amount of binding agent, a decrease of metabolism with amount of binding agent indicating that cytochrome P450 2C family member metabolizes the compound. In some such methods, the compound is contacted with cytochrome P450 2C family member in a sample containing a collection of cytochrome P450 enzymes including the 2C family member. A preferred P450 2C family member is P450 2C 2C19.

In some methods, the sample is a tissue sample. In some methods, the collection of enzymes are obtained from a cell culture expressing the enzymes. In some methods, the compound is a drug, steroid or carcinogen.

The invention further provides methods of detecting cytochrome p450 2C members. Such methods entail contacting a sample suspected of containing cytochrome P450 2C family member with a binding agent described above. One then determines whether the agent specifically binds to the sample, specific binding indicating the presence of the particular cytochrome P450 2C family member in the sample.

The invention further provides methods of measuring P450 2C levels in an individual relative to P450 levels in a control population. Such methods entail contacting a sample suspected of containing cytochrome a P450 2C family member from the individual and a substrate of 2C. One then determines the p450 2C levels in the individual relative to P450 2C levels in the control population.

DETAILED DESCRIPTION OF THE INVENTION

Figure 1:
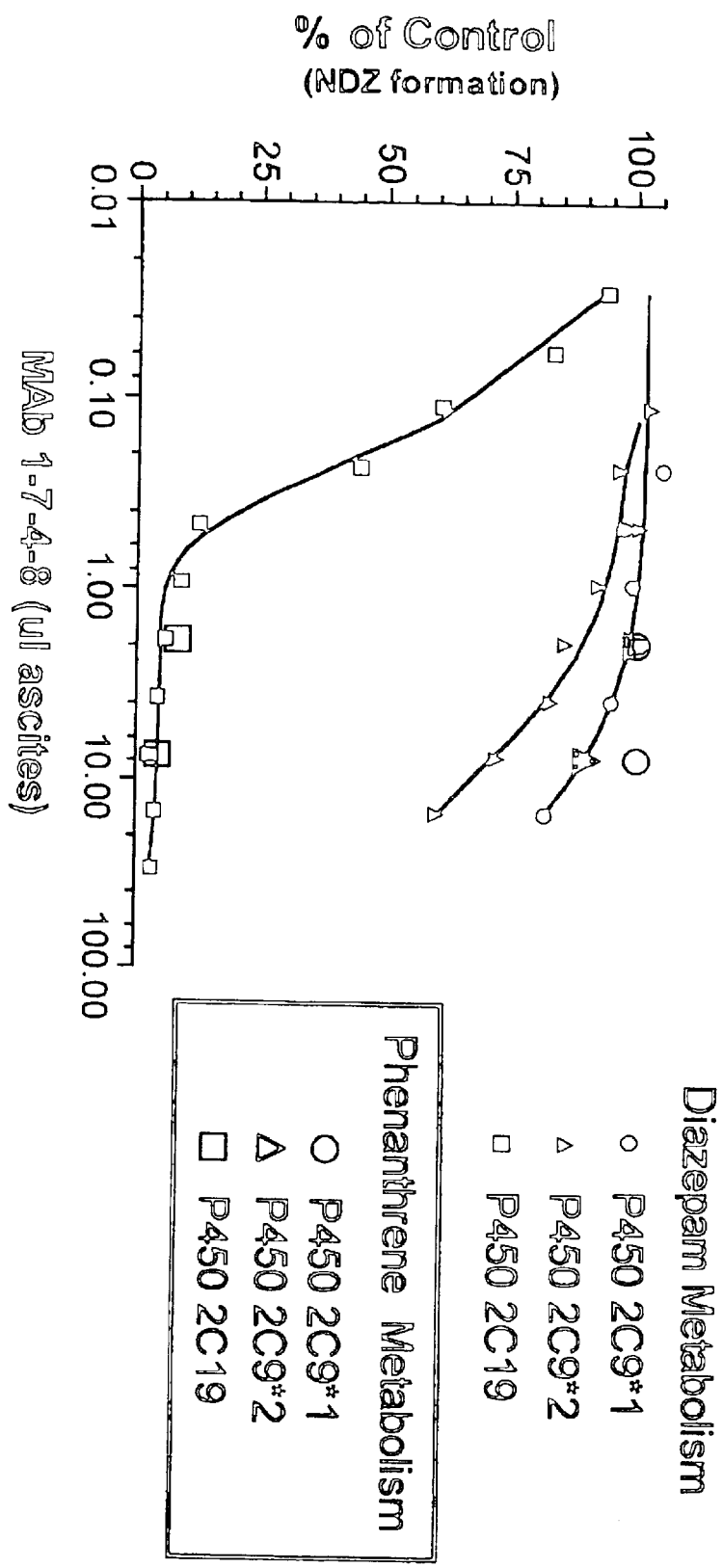
FIG. 1. Inhibition of diazapam and phenanthrene metabolism by monoclonal antibodies MAb 1-7-4-8, MAb 1-5-1-3, and MAb 1-1-11-1.

The invention provides monoclonal antibodies and other binding agents in isolated form that specifically bind to human cytochrome P450 2C19, and inhibit enzymic activity of 2C19. Preferred agents lack specific binding to other human cytochromes P450. The invention further provides methods of using the antibodies and other binding agents in identifying individuals with a deficient metabolizing 2C19 phenotype, and in screening drugs for metabolism by cytochrome P450 2C19.

Except when noted, the terms "patient" or "subject" are used interchangeably and refer to mammals such as human patients and non-human primates, as well as experimental animals such as rabbits, rats, and mice, and other animals.

Specific binding between an antibody or other binding agent and an antigen means a binding affinity of at least $10^6$ $M^{-1}$. Preferred binding agents bind human cytochrome P450 2C19 with affinities of at least about $10^7 M^{-1}$, and preferably $10^8 M^{-1}$ to $10^9 M^{-1}$ or $10^{10} M^{-1}$.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "antibody" includes intact antibodies, antigen-binding portions of an intact antibody and binding fragments thereof that retain capacity to bind P450 2C19.

The terms "monoclonal antibody" (also referred to as "Mab" or "MAbs") and "monoclonal antibody composition" refer to a preparation of antibody molecules of single molecular composition. A monoclonal antibody composition displays a single binding specificity and affinity for a particular epitope.

The term "polyclonal antibody" refers to a preparation of more than 1 (two or more) different antibodies to human cytochrome P450 2C19. Such a preparation includes antibodies binding to a range of different epitopes.

The term "Ka", as used herein, is intended to refer to the equilibrium association constant of a particular antibody-antigen interaction. This constant has units of 1/M.

The term "Kd", as used herein, is intended to refer to the equilibrium dissociation constant of a particular antibody-antigen interaction. This constant has units of M.

The term "ka", as used herein, is intended to refer to the kinetic association constant of a particular antibody-antigen interaction. This constant has units of 1/Ms The term "kd", as used herein, is intended to refer to the kinetic dissociation constant of a particular antibody-antigen interaction. This constant has units of 1/s.

The phrase "substantially identical," in the context of two nucleic acids or polypeptides (e.g., DNAs encoding a humanized immunoglobulin or the amino acid sequence of the humanized immunoglobulin) refers to two or more sequences or subsequences that have at least about 80%, most preferably 90–95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering scheme in Kabat. Therefore, for antibodies, percent identity has a unique and well-defined meaning. That is, percent sequence identity is the percentage of aligned amino acids or nucleotides that are the same between two immunoglobulins or their coding sequences being compared.

Amino acids from the variable regions of the mature heavy and light chains of immunoglobulins are designated Hx and Lx respectively, where x is a number designating the position of an amino acids according to the scheme of Kabat et al., 1987 and 1991, Sequences of Proteins of Immunological Interest (National Institutes of Health, Bethesda, Md.). Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

An isolated species means an object species (e.g., a binding polypeptide of the invention) that is the predominant species present (i. e., on a molar basis it is more abundant than any other individual species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

I. Binding Agents of the Invention

A. Specificity and Functional Properties

Binding agents of the invention compete with exemplary antibodies designated MAb 1-7-4-8 (ATCC PTA-3970, MAb 1-5-1-3, (ATCC PTA-3969 and MAb 1-1-11-1 (ATCC PTA-3971 for specific binding to human cytochrome P450 2C19. Production of monoclonal antibodies MAb 1-7-4-8, MAb 1-5-1- 3, MAb 1-1-11-1 is described in the Examples. The data in the Examples show that out of the total repertoire of antibodies to human cytochrome P450 2C19, only a small proportion inhibit 2C19 enzymic activity. Binding agents that compete with MAb 1-7-4-8,MAb 1-5-1-3, and MAb 1-1-1 1-1 for binding to cytochrome P450 2C19 are expected to share similar inhibitory properties because inhibition by the exemplified antibodies likely arises through binding of the exemplified antibodies to an active site of 2C19,and competing agents bind to the same or closely proximate site as MAb 1-7-4-8, MAb 1-5-1-3, and MAb 1-1-11-1. Capacity to compete with MAb 1-7-4-8, MAb 1-5-1-3, and MAb 1-1-11-1, thus defines a select subclass of antibodies with advantageous properties from the total repertoire of antibodies to human cytochrome P450 2C19.

Hybridomas producing MAb 1-7-4-8 (ATCC PTA-3970, MAb 1-5-1-3, (ATCC PTA-3969 and MAb, 1-1-11-1 (ATCC PTA-3971 have been deposited with the American Type Culture Collection, 10801 University Boulevard, Manassas, Va. 20110-2209 under the Budapest Treaty and given the Accession Nos. indicated on Jan. 8, 2001. These cell lines will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Competition is determined by an assay in which the antibody under test inhibits specific binding of a reference antibody to an antigenic determinant on human cytochrome P450 2C19. Numerous types of competitive binding assays are known for example: (See Harlow and Lane, 1988, "Antibodies, A Laboratory Manual," Cold Spring Harbor Press). Typically, such an assay involves the use of purified human cytochrome P450 2C19, an unlabelled test antibody and a labeled reference antibody. Competitive inhibition is measured by determining the amount of label bound to human cytochrome P450 2C19 in the presence of the test antibody. Usually the test antibody is present in excess. Antibodies identified by competition assay (competing antibodies) include antibodies binding to the same epitope as a reference antibody and antibodies binding to an adjacent epitope sufficiently proximal to the epitope bound by the reference antibody for steric hindrance to occur. Usually, when a competing antibody is present in excess, it will inhibit specific binding of a reference antibody to human cytochrome P450 2C19 by at least 10, 25, 50, 75, 80, 90, or 95%.

Binding agents of the invention typically lack specific binding (i.e., crossreactivity) to human cytochromes P450 other than 2C19, so that the binding agents can be used to detect human cytochrome P450 2C19 in the presence of other cytochromes P450. For example, binding agents of the invention typically lack specific binding to one or more of human cytochromes P450 1A1, 1A2, 1B1, 2A6, 2B6, 2C8, 2C9*1, 2C9*2, 2C9*3, 2C 18, 2D6, 2E1, 3A4, and 3A5 as measured by ELISA and immunoblot. Some binding agents of the invention, including the exemplified MAb 1-7-4-8, MAb 1-5-1-3, and MAb 1-1-11-1 lack specific binding to all of the above human cytochromes P450.

As noted above, binding agents of the invention are characterized by capacity to inhibit human cytochrome P450 2C19-catalyzed metabolism of a substrate known to be metabolized by the enzyme. The enzyme can be assayed with any of phenacetin, 7-ethoxycoumarin, chlorzoazone or phenanthrene as the substrate (See present Examples). Assays can be performed in either a microsome systems or a reconstituted systems of purified enzymes. For example, a suitable microsome system contains 1 mg/mL protein of human liver microsomes or 1.6 mg protein/mL from human lymphoblast cell lines, together with 0.2 mM substrate in a final volume of 1.0 mL of 100 mM potassium phosphate buffer, pH 7.5, and 1 mM NADPH. An exemplary reconstituted system, in place of the microsome system, contains about 20–50 nM purified human P450 2C19, 40–100 nM cytochrome b5, 100 nM NADPH-P450 reductase, 10 µg/mL phospholipids and 0.25 mM sodium cholate. Incubations are typically carried out at 37° C. for 30 min. Percentage inhibition is defined as 1-(rate of formation metabolic product in presence of test antibody/rate of formation of metabolic product in presence of control antibody), when antibody is present in excess. (The control antibody is an antibody lacking specific binding to human cytochrome P450 2C19.) Some agents of the invention inhibit metabolic capacity of isolated pure cytochrome P450 2C19 on any or all of the above substrates by at least 25%, 50%, 75%, 85%, 90% or 95% or more.

B. Antibodies of the Invention

1. General Characteristics

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, FUNDAMENTAL IMMUNOLOGY (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., 1987, *J. Mol. Biol.* 196: 901–917;, *Nature*, 1989, 342: 878–883; and J. Mol. Biol., 1989, 186: 651–663.

2. Production

Antibodies to human cytochrome P450 2C19 can be produced by a variety of means. The production of non-human monoclonal antibodies, e.g., murine or rat, can be accomplished by, for example, immunizing the animal with a preparation containing purified human cytochrome P450 or a fragment thereof. The immunogen can be obtained from a natural source, by peptides synthesis or preferably by recombinant expression. Antibody-producing cells obtained from the immunized animals are immortalized and screened for the production of an antibody which binds to human cytochrome P450 or a fragment thereof. See Harlow & Lane, Antibodies, A LABORATORY MANUAL (CSHP New York, 1988) (incorporated by reference for all purposes).

Humanized forms of mouse antibodies can be generated by linking the CDR regions of non-human antibodies to human constant regions by recombinant DNA techniques. See Queen et al., *Proc. Natl. Acad. Sci. USA* 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to human cytochrome P450 or a fragment thereof. Human antibodies are selected by competitive binding experiments, or otherwise, to have the same epitope specificity as a particular mouse antibody, such as MAb 1-7-4-8,MAb 1-5-1-3, and MAb 1-1-11-1. Such antibodies are particularly likely to share the useful functional properties of the exemplified antibodies.

3. Antibody Fragments

Antibodies of the invention include intact antibodies and fragments. Typically, these fragments compete with the intact antibody from which they were derived for specific binding to human cytochrome P450 2C19, and bind with an affinity of at least $10^6$ $M^{-1}$, $10^7$ $M^{-1}$, $10^8$ $M^{-1}$, $10^9$ $M^{-1}$, or $10^{10}$ $M^{-1}$. Antibody fragments include separate heavy chains, light chains Fab, Fab' F(ab')2, Fv, and single chain antibodies comprises a heavy chain variable region linked to a light chain variable region via a peptide spacer. Fragments can be produced by enzymic or chemical separation of intact immunoglobulins. For example, a F(ab')2 fragment can be obtained from an IgG molecule by proteolytic digestion with pepsin at pH 3.0–3.5 using standard methods such as those described in Harlow and Lane, supra. Fab fragments may be obtained from F(ab')2 fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This maimer of expression is advantageous for affinity-sharpening of antibodies.

4. Recombinant Expression of Antibodies

Nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host particularly for expressing antibodies of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies of the present invention (See Winnacker, 1987, FROM GENES TO CLONES (VCH Publishers, N.Y.). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., 1977, *J. Gen. Virol.* 36:59); baby hamster kidney cells (BHK, ATCC CCL 10); Chinese hamster ovary-cells-DHFR (CHO, Urlaub and Chasin, 1980, *Proc. Natl. Acad. Sci. USA* 77:4216); mouse sertoli cells (TM4, Mather, 1980, *Biol. Reprod.* 23:243–251); monkey kidney cells (CV1 ATCC CCL 70); African green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., 1982, *Annals N.Y Acad. Sci.* 383:44–46); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. (See generally Sambrook et al., 1989, MOLECULAR CLONING: A LABORATORY MANUAL (Cold Spring Harbor Press, 2nd ed.) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i. e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (See generally SCOPES, PROTEIN PURIFICATION (Springer-Verlag, N.Y., 1982). Substantially pure immunoglobulins of at least about 90 to 95% homogeneity are preferred, and 98 to 99% or more homogeneity most preferred.

5. Screening for Sequence Analogs

Many of the antibodies described above can undergo non-critical amino-acid substitutions, additions or deletions in both the variable and constant regions without loss of binding specificity or effector functions, or intolerable reduction of binding affinity (i. e., below about $10^6$ $M^{-1}$ for human cytochrome P450 2C19. Usually, the light and heavy chain variable regions of immunoglobulins incorporating such alterations exhibit at least 80, 90 or 95% sequence identity to the corresponding regions of a reference immunoglobulin from which they were derived, such as MAb 1-7-4-8, MAb 1-5-1-3, and MAb 1-1-11-1. Preferred antibody light and heavy chain sequence variants have the same complementarity determining regions (CDRs) as the corresponding chains from one of the above reference antibodies. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; Huse, WO 92/06204.

C. Other Binding Agents of the Invention

The invention further provides nonantibody binding agents that compete with one of the exemplified antibodies for binding to human cytochrome P450 2C19. These binding agents include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. The libraries of compounds are screened for binding to human cytochrome P450 in competition with one of the reference antibodies MAb 1-7-4-8, MAb 1-5-1-3, and MAb 1-1-11-1.

II. Human Cytochrome P450 2C19

The cDNA for human cytochrome P450 2C 19 has been cloned, sequenced, and expressed (see e.g., Goldstein et al., 1991, Biochemistry 30:3247–55). Sources of other cytochromes P450 (e.g., for use in testing for lack of crossreactivity) are described by Nebert, 1991, *DNA & Cell Biol.* 10, 1–14; Nelson et al., 1996, *Pharmacogenetics* 6, 1–42). Insect cells (e.g., SF9) with appropriate vectors, usually derived from baculovirus, are also suitable for expressing 1A2 and other cytochromes P450. See Luckow et al., 1988, *Bio/Technology* 6:47–55; Gonzalez et al., 1991, *Meth. Enzymol.*, 206, 93–99 (incorporated by reference for all purposes). Other expression systems include yeast (Ellis et al., supra), *E. coli* (Gillam et al., 1995, *Archives Biochem. Biophys.* 319, 540–550; vaccinia virus (Gonzalez, 1989, *Pharmacol. Res.* 40, 243, and human AHH-1 lymphoblastoid cells (Crespi et al., 1989, *Carcinogenesis* 10, 295–301).

Humans shows a wide range of 2C19 activities. Variations of P450 activity in a tissue can result from a variety of factors including nutritional factors, chemical inducers in the environment, age, sex and general physiological or disease condition of the subject individual. MAbs to 2C19 can define the P450 variations related to genetic, age, sex, nutritional and environmental influences on P450 metabolism. The role in the metabolism of a drug by a single or multiple P450s can be important in drug discovery for understanding P450 dependent partner drug relationships that can be toxic. The P450s can be major control elements of the metabolic rates of drug metabolism as well as their pharmacologic character. The MAbs can also identify drugs toxic due to the absence of a polymorphic P450. This information can lead to better understanding of P450 activity in drug choice, dosage and efficacy.

Several therapeutically important compounds are metabolized by 2C19. The list includes S-mephenytoin, diazepam, diclofenac, mephenytoin, tolbutabmide, bufuralol, imipramine, omeprazole, hexobarbital, and proguanil.

III. Methods of Use
A. Identifying Compounds Metabolized By P450 2C19

Binding agents of the invention that inhibit enzymic activity of human cytochrome P450 2C19 can be used to assay whether compounds are metabolized by 2C19. Compounds include xenobiotics, such as a currently used and new drugs, carcinogens, pesticides or other industrial or environmental chemicals, or any endobiotic, such as a steroid E hormone. The assay can indicate not only that a compound is metabolized by 2C19 but also the contribution of 2C 19 to metabolizing the compound relative to other cytochromes P450 present in microsomes or cell homogenates.

Assays are performed by contacting a compound under test with human cytochrome P450 2C19 in reaction mixtures containing varying amounts of a binding agent of the invention. For example, two separate reactions may be set up, one in which the binding agent of the invention is present, and the other, a control in which the binding agent is absent. The human cytochrome P450 is often present as a microsomal extract from human or animal cells or cell lines or an extract from cell cultures expressing a collection of recombinant P450s including 2C19. The assay is performed under conditions in which 2C19 is known to be active on known substrates, such as phenanthrene (See Examples). Metabolism of the compound under test is then followed from the disappearance of the compound or appearance of a metabolic product of the compound as a function of time (e.g., nmol product/sec). See, e.g., Buters et al., 1994, *Drug Metab. Dispos.* 22: 688. The metabolism of the compound is analyzed as a function of the amount of binding agent present. If the metabolism quantitatively decreases with amount of binding agent, it can be concluded that 2C 19 metabolizes the compound.

The percentage inhibition of 2C19 metabolism of a test compound may reflect both the inherent efficiency of a binding agent in blocking 2C19 activity and the contribution of cytochromes P450 other than 2C19 in metabolizing the compound. The inherent blocking efficiency of a binding agent can be determined by measuring inhibition of metabolism in a reaction mixture in which only 2C19 is present, or alternatively, in a reaction mixture in which a collection of cytochromes P450 are present but the substrate is known to be metabolized only by 2C19. Comparison of the percentage inhibition determined in these circumstances with the percentage inhibition of metabolism of a test substrate when a mixture of cytochromes P450 are present indicates the relative contributions of 2C19 and other enzymes in the mixture to metabolism of the test substrate. For example, if metabolism of a control substrate by pure 2C19 is inhibited by a binding agent by 90% and metabolism of a test substrate by a mixture of cytochromes P450 including 2C19 is inhibited 45%, it can be concluded that in the mixture, 2C19 contributes about 45/90=50% of metabolizing activity on the test substrate. Binding agents having a high degree of inhibition (e.g., at least about 90%) of a known substrate are particularly effective for quantitative analysis as described above.

The anti 2C19 Mab can also be used to identify substrates metabolized by CYP2C19 in human liver tissues. Recognition of the nature and contribution of CYP2C19 in individuals can permit studies of drug-drug interactions based on competitive metabolism. MAb 1-7-4-8, MAb 1-5-1-3, and MAb 1-1-11-1 can also be used as reagents for CYP2C19 based metabolism studies of procarcinogens and promutagens. These MAbs can also be used in drug metabolism studies for understanding drug disposition, activation and therapeutic applications.

Information made available by the above methods can be exploited in a number of applications. Drugs determined to be processed by 2C19 should in general not be prescribed to patients deficient in 2C19 metabolism, or should be prescribed in reduced amounts or with close monitoring. Particular caution is needed in combination therapies involving two drugs metabolized by the 2C19 pathways. The information can also be valuable in drug design and screening. That is drugs can be designed or screened such that they are metabolized to a significant extent by several P450 enzymes, and are not therefore likely to cause side effects in those deficient in any single enzymes. Recognition that a carcinogen or other environmental toxin is deactivated by 2C19 signals that deficient metabolizers are at particular risk from the carcinogen or compound. Conversely, recognition that a carcinogen or other environmental toxin is activated to harmful form by 2C19 indicates that deficient metabolizers are less prone to harm from exposure to such a compound relative to extensive metabolizers.

B. Use of Agents for Diagnosing P450 Metabolic Variations

The binding agents are useful diagnostics to determine a patient's metabolic profile prior to treatment with a drug known or suspected to be metabolized by 2C19. Patients identified as defective in 2C19 metabolism can be given alternative therapy, a lower dosage or additional monitoring to avoid damaging side effects from their DM phenotype. Diagnosis can be performed as described below.

1. Binding Assay

Binding agents of the invention are useful for the quantitative measurement of the amount of individual P450 proteins in a sample, which may contain multiple forms of other P450 proteins. Binding between binding agent and cytochrome P450 2C19 in the sample can be detected by radioimmunoassay, ELISA or immunoblotting (see Harlow and Lane, supra). The type of immunoassay can be tailored to the particular application. In radioimmunoassay, the binding agent of the invention is typically labeled. In ELISA, the binding agent is typically unlabelled and detected using a secondary labeled reagent with affinity for the binding agent (e.g., anti-IgG $^{35}$S-or $^{3}$H-labeled MAb). Immuno blots are particularly useful for screening a sample with a panel of antibodies to different cytochromes P450.

These assays can be tailored to measure P450 2C19 levels in an individual relative to P450 2C19 levels in a control population. The method entails contacting a sample suspected of containing cytochrome P450 2C19 from the individual with a 2C19 substrate. One then determines the P450 2C19 levels in the individual relative to the 2C19 levels in a control population.

Other Uses

The binding agents of the invention can also be used for affinity purification of cytochrome P450 2C19. The basic procedure for affinity purification requires only one or two steps and can yield highly purified milligram quantities of cytochrome P450 2C19. For example, the binding agent can be covalently bound to Sepharose™, which is made into the form of either column or a slurry for batch purification. A sample containing cytochrome P450 2C19 is them passed through the column or slurry and binds to the binding agent-linked Sepharose™. The nonbound material containing unrelated proteins and cytochromes P450 other than 2C19 are thoroughly eluted leaving the cytochrome P450 2C19, which can then be eluted and used for a variety of chemical and physical studies. See, e.g., Cheng et al., 1948, *J. Biol. Chem.* 259, 12279–12284.

Monoclonal antibody based immunohistochemical methods can be applied to localize and examine the distribution cytochrome P450 2C19 after different inducer administration, during various physiological states related to nutrition, age, and sex, and in different species and tissues. Furthermore, the intracellular distribution of the cytochrome P450 2C19 can be determined in a way not possible by standard biochemical methods which generally cannot identify the presence of specific forms of cytochrome P450 proteins in isolated tissues and organelles. See, e.g., Gelboin, 1993, *Pharmacol. Rev.* 45, 413–453.

Variations of P450 activity in a tissue can result from a variety of factors including nutritional factors, chemical inducers in the environment, age, sex and general physiological or disease condition of the subject individual. MAbs to 2C19 can define the P450 variations related to genetic, age, sex, nutritional and environmental influences on P450 metabolism. The role in the metabolism of a drug by a single or multiple P450s can be important in drug discovery for understanding P450 dependent partner drug relationships that can be toxic. The P450s can be major control elements of the metabolic rates of drug metabolism as well as their pharmacologic character. The MAbs can also identify drugs toxic due to the absence of a polymorphic P450. This information can lead to better understanding of P450 activity in drug choice, dosage and efficacy.

EXAMPLES

Materials and Methods

Chemicals

Tolbutamide, diclofenac, diazepam, phenanthrene and NADPH were obtained from Sigma (St. Louis, Mo.). Taxol (paclitacel), 6α-hydroxytaxol, S-mephenytoin, 4'-hydroxymephenytoin, bufuralol, 1'-hydroxybufuralol, hydroxytolbutamide and 4'-hydroxydiclofenac were obtained from Gentest Corporation (Woburn, Mass.). Imipramine and desipramine were obtained from ICN Biomedicals Inc. (Aurora, Ohio). All reagents were of analytical grade. Nordiazepam was a gift from Dr. Shen Yang. 2-hydroxyimipramine was a gift from Novartis Pharmaceuticals.

P450 Expression and Hybridoma Production

P450 2C9 recombinant baculovirus was previously constructed (Grogan et al., 1995) with cDNA P450 2C19 (a kind gift from Dr. Joyce Goldstein, NIEHS, NIH, Research Triangle Park, N.C.) and cDNA P450 2C8 (Kimura et al., 1987) and were inserted into baculovirus transfection vectors (MaxBac 2.0 transfer vectors and Bac-N-Blue transfection kit, Invitrogen, Inc., Carlsbad, Calif. ). The resulting recombinant baculovirus was used to express the P450s in Sf9 (*Spondoptera frugipedra*) cells. Cells (1.0×10$^6$/mL) were infected with the recombinant virus (MOI=1–5) and supplemented with 1 μg/mL heme-albumin complex (Grogan et al., 1995). Three days post infection, cells were havested, the P450 difference spectrum measured, and the cells were stored at −80° C. The P450 was extracted from the cells as previously described (Gelboin et al., 1998). Yielding 268.0 nanomole P450 2C8, 22.5 nanomole P450 2C9, and 60.5 nanomole P450 2C19 each from one liter of individual cell culture preparations.

The extracted expressed P450 was used as the immunogen. Balb/c mice were immunized with 30–50 μg of extracted P450 2C8, 2C9 or 2C19 emulsified in 0.2 mL adjuvant once a week for three weeks, sacrificed and the spleen cells isolated. The complete immunization technique and hybridization of spleen cells with myeloma cells (NS-1) has been detailed (Gelboin et al., 1998). Three mice were used for each immunization. The resulting hybridomas were screened by ELISA using the same extracted material described above. Extracted material from SF9 cells infected with wild type baculovirus was used to test for specific binding of the antibodies to the immunogen. Hybridomas producing antibodies that bound to wild type material were discarded.

The cDNA expressed human P450 enzymes used for immuno-assays and metabolic inhibition assays were obtained from vaccinia infected HepG2 cells (Battula et al., 1987) (Gonzalez and Korzekwa, 1995), Supersomes (Gentest, Woburn, Mass.), and/or Baculosomes (Panvera Corporation, Madison, Wis.). Human liver samples were provided by the Cooperative Human Tissue Network (CHTN) funded by the National Cancer Institute. Microsomes from human liver were prepared as described (Alvares et al., 1970), and total P450 content measured by difference spectra (Omura and Sato, 1964). Protein content was measured with BCA Protein Assay Kit (Pierce, Rockford, Ill.) using BSA as a standard.

Immunoassays

ELISA was performed by a generally used method (Harlow and Lane, 1988). 96-well plates were coated with 1.5 picomole of P450 enzyme. Culture fluid and/or diluted ascites was used as the primary MAb, with an alkaline phosphatase conjugated anti-mouse IgG (Fc specific) (Jackson Immuno-Research, West Grove, Pa.) used as a secondary antibody. Colorimetric assays were measured at 405 nm wavelength as detailed (Krausz et al., 2000). Wells with an optical density (O.D.) reading ≧0.6 with specific immunogen and an O.D. ≦0.1 with wild type antigen were investigated further. All resulting specific hybridomas were cloned at least three times. SDS-PAGE gels and immunoblots (IB) were performed as previously described (Gelboin et al., 1996). MAb isotyping was performed using radial immunodiffusion kits purchased from "The Binding Site" (San Diego, Calif.). All MAbs described are mouse IgG$_1$, with the exception of MAb 1-68-11, which is a mouse IgM.

Metabolic Incubations

Metabolism and immunoinhibition studies were performed using cDNA expressed P450 enzymes and human liver microsomes (HLM). Metabolic incubations were generally conducted as follows: 0.057 to 30 µl (1.2 to 1000 µg) of ascites protein containing MAb was pre-incubated with 30–50 pmole of expressed P450 enzyme or 150–300 pmol P450 in HLM in 0.5 mL of buffer (100 mM Tris pH 7.5) at 37° C. for 5 minutes. Substrate (in 10 µl methanol), 1 mM NADPH, and additional buffer were added to a final volume of 1.0 mL. The reactions were allowed to proceed for 60 minutes with the tolbutamide, and S-mephenytoin; 15 minutes with diclofenac and 30 minutes with phenanthrene, diazepam, imipramine, and bufuralol and stopped with 1 mL acetone. The metabolites were extracted with 8 mL dichloromethane and subjected to HPLC separation conditions for diclofenac (50 µM) to 4'-hydroxydiclofenac (Crespi and Penman, 1997), tolbutamide (200 µM) to hydroxytolbutamide (Relling et al., 1990), S-mephenytoin (150 µM) to 4'-hydroxymephenytoin (Heyn et al., 1996), diazepam (150 µM) to nordiazepam (Yang et al., 1998c), imipramine (200 µM) to desipramine and 2-hydroxyimipramine (Yang et al., 1999), taxol (150 µM) to 6α-hydroxytaxol (Rahman et al., 1994), phenanthrene (200 µM) to 9,10-diol and 9-phenol (Yang et al., 1999), and bufuralol (50 µM ) to 1'-hydroxybufuralol (Gelboin et al., 1997) are previously described. HPLC was performed using a Hewlett Packard Model 1050 Series system equipped with an autosampler, a quaternary solvent delivery system, and a dioarray detector controlled by the Hewlett Packard Chemstations software. Metabolite retention times were compared with authentic standards (when available) and metabolite peaks were quantitated based on ratios with internal standards. Control incubations contained an MAb against hen egg white lysozyme (MAb HyHel-9) to assess for nonspecific reactions. Percent of inhibition was calculated based on activity in the presence of the specific MAb relative to the activity with the control MAb. Percent inhibition equals 100 minus % of control. Data is the mean of duplicate incubations using expressed enzymes, and triplicate incubations using HLM.

Inhibition of phenanthrene metabolism to 9,10-diol was used to test for inhibitory cross reactivity of the MAbs with expressed P450 1A1, 1A2, 2B6, 2C8, 2C9, 2C18, 2C19, 2E1, 3A4, and 3A5; inhibition of phenanthrene metabolism to the 9-phenol was assayed for cross-reactivity with P450 2A6; and inhibition of bufuralol metabolism to 1'-hydroxybufuralol was assayed for cross-reactivity with P450 2D6. Inhibition of diazepam conversion to nordiazepam (NDZ) was also used to test the inhibitory cross-reactivity of the MAbs among the P450 2C isoforms.

Isolation and Screening of Hybridomas and Monoclonal Antibodies

MAbs to P450 2C8

MAbs from 830 hybridoma clones produced 16 MAbs that bound to 2C8. Three of the 16 hybridoma clones produced MAbs that bound specifically and strongly to only 2C8. The three MAbs were 281-1-1, 13-1-3 and 5-1-5 which were both specific and strong inhibitors (90%) of expressed 2C8 enzyme activity. The three MAbs also immunoblot 2C8.

MAbs specific to individual P450 2C9, 2C19 and to isoform sets of the 2C sub-family Screening for MAbs to 2C9: MAbs produced from 1088 hybridomas were screened and 68 clones were identified that bound to 2C9. Six of the 68 bound strongly and inhibited 2C9 enzyme activity. Further screening resulted in the isolation of MAb 763-15-5, specific and highly inhibitory to 2C9 at low levels of MAb. MAbs from other clones were isolated and characterized and found to bind and inhibit unique sets of 2C sub-family isoforms as detailed in the Results below. The binding of a MAb to more than one isoform detects an epitope common to the various target isoforms. (See Results, Tables 1–7).

Another MAb resulting from immunization with 2C9*2 was MAb 292-2-3. The details of its isolation have been previously described (Krausz et al., 2000) and its further characterization are described in the Results. Previously Mab 1-68-11 was made with purified rat liver 2c/RLM5 (Park et al., 1989) which was subsequently found to inhibit all four of the human 2C isoforms, 2C8, 2C9, 2C18 and 2C19 (Gelboin et al., 1997)

Screening for MAbs to 2C19: The screening for binding of MAbs formed from 763 hybridoma clones detected the binding to 2C19 MAbs from 15 to clones. Three of the latter MAbs strongly and specifically bound and inhibited 2C19 metabolic activity. These are MAb 1-7-4-8, MAb 1-5-1-3 and MAb 1-1-11-1 and are further discussed below.

Results

The specificity of MAb 1-7-4-8, MAb 1-5-1-3, and MAb 1-1-11-1 was determined with expressed P450 2C19 as measured by ELISA binding (Table 1). The three MAbs bind specifically and strongly to P450 2C19 as measured by ELISA and do not bind to the twelve other drug metabolizing human P450 members (P450 1A1, 1A2, 1B1, 2A6, 2B6, 2C8, 2C9*1, 2C9*2, 2C9*3, 2C18, 2D6, 2E1, 3A4, and 3A5) (see Table 1 below).

TABLE 1

Specificity of Monoclonal Antibody Binding to Expressed P450 2C19 as Measured by ELISA

| Mab/P450 | 2C8 | 2C9*1 | 2C9*2 | 2C9*3 | 2C18 | 2C19 | 1A1, 1A2, 2A6, 2B6, 2D6, 2E1, 3A4, 3A5 |
|---|---|---|---|---|---|---|---|
| MAb 1-7-4-8 | 0.0+ | 0.14 | 0.0 | 0.15 | 0.0 | 1.20 | 0.0 |
| MAb 1-1-11-1 | 0.0 | 0.20 | 0.14 | 0.12 | 0.0 | 1.41 | 0.0 |
| MAb 1-5-1-3 | 0.0 | 0.19 | 0.28 | 0.11 | 0.0 | 1.16 | 0.0 |

+Values equal absorbance at 405 nm.

Mab 1-7-4-8, Mab 1-5-1-3, and Mab 1-1-11-1 do not immunoblot (IB) their target P450 2C19. The mmetabolism of two substrates of the 2C family members, phenanthrene (Shou et al., 1994; see Table 2A below) or diazepam (see Table 2B below) were used to measure the inhibitory activity of Mab 1-7-4-8, Mab 1-5-1-3, and Mab 1-1-11-1

Table 2A and B

Specificity of Inhibitory Activity of MAbs Anti-P450 2C19 for Phenanthrene (A) and Diazepam (B) Metabolism

TABLE 2A

% INHIBITION OF PHENANTHRENE^ METABOLISM

| | P-450 | 1A1 | 1A2 | 1B1 | 2A6 | 2B6 | 2C8 | 2C9*1 $Arg_{144}$ | 2C9*2 $Cys_{144}$ | 2C18 | 2C19 | 2D6 | 2E1 | 3A4 | 3A5 |
|---|---|---|---|---|---|---|---|---|---|---|---|---|---|---|---|
| MAbs Anti-2C19 | 1-7-4-8 | —** | — | — | — | — | — | — | —# | —# | — | 97.6 | — | — | — | — |
| | 1-1-11-1 | — | — | 7.8 | — | — | — | — | —# | —# | — | 97.5 | — | — | — | — |
| | 1-5-1-3 | — | — | — | — | — | — | — | —# | —# | — | 97.5 | — | — | — | — |

^formation of 9–10 diol was measured except for 2A6, where 9-phenol was measured, and 2D6, where bufurolol was used as the substrate and 1-OH bufurolol was measured.
**(−) indicates <1.5% inhibition.
the MAbs specifically and strongly inhibit (>95%) P450 2C19 at optimal MAb concentration. At higher levels of MAb (greater than 4-fold) there is a slight cross-reaction with P450 2C9. (See FIG. 1)

TABLE 2B

% INHIBITION OF DIAZEPAM+ METABOLISM

| | P-450 | 1A1 | 1A2 | 1B1 | 2A6 | 2C19 |
|---|---|---|---|---|---|---|
| MAbs Anti-2C19 | 1-7-4-8 | —** | —# | —# | — | 97.6 |
| | 1-1-11-1 | — | —# | —# | — | 97.5 |
| | 1-5-1-3 | — | —# | —# | — | 97.5 |

+formation of diazepam N-demethylation (NDZ) was measured.
**(−) indicates <1–10% inhibition.
the MAbs specifically and strongly inhibit (>95%) P45 2C19 at optimal concentration. At higher levels of MAb (greater than 4-fold) there is a slight cross-reaction with P450 2C9. See FIG. 1

The data in Table 2A and B show the inhibitory activity of the MAbs toward the 2C family-catalyzed metabolism. The inhibition of phenanthrene metabolism for 2C19 was greater than 97%. The inhibition of diazepam metabolism was also greater than 97%. The three MAbs are thus sensitive and precise probes for measuring 2C19-catalyzed metabolism in liver and other tissues.

MAb 1-7-4-8 is an extremely strong inhibitor of 2C19 enzyme activity when added even at a low level of 0.5 $\mu$l of ascites fluid (>95%) (see FIG. 1). MAb 1-7-4-8 shows slight inhibitory cross reactivity to 2C9, less than 20% when added at a very high level of 6.0 $\mu$l of ascites. (FIG. 1, Tables 1 and 2). Similar cross-reaction was observed with MAb 1-1-11-1 and MAb 1-5-1-3.

Thus, at very high concentrations, there is a slight (up to 30%) inhibition of P450 2C9. However, this cross-reactivity is eliminated and 95% inhibition of P450 2C19 is maintained when optimal concentrations of the MAbs are used.

The amino acid sequence identity among the P450 2C family (2C8, 2C9, 2C18 and 2C19) is greater than 77%, with 2C9 and 2C19 homology at 91%. Thus the subject MAbs detect and target P450 2C19, an isoform closely related structurally to the other 2C isoforms. The extraordinary specificity of the MAbs is unique and not exhibited by any other antibody or chemical probe.

The single and the combinatorial use of the MAbs can "reaction phenotype", i.e., determine the metabolic contribution and interindividual variation of a P450 isoform for the metabolism of a drug or non-drug xenobiotic in human liver microsomes. The utility of the MAb based analytic system was examined with the model substrates: taxol, diazepam, tolbutamide, diclofenac, mephenytoin and imipramine. The MAb system can identify drugs metabolized by a common P450 or several P450s and polymorphic P450s. The MAb system identifies drugs or drug metabolic pathways that are catalyzed by a single P450 and thus can be used for in vivo phenotyping. The MAb system can identify whether a particular drug is metabolized by a single P450 that may exhibit polymorphic expression in humans. The MAb system offers large potential for studies of cytochrome P450 function useful in Drug Discovery and reduce the possibility of adverse drug reactions due to polymorphisms and drug interactions.

Figure 2:
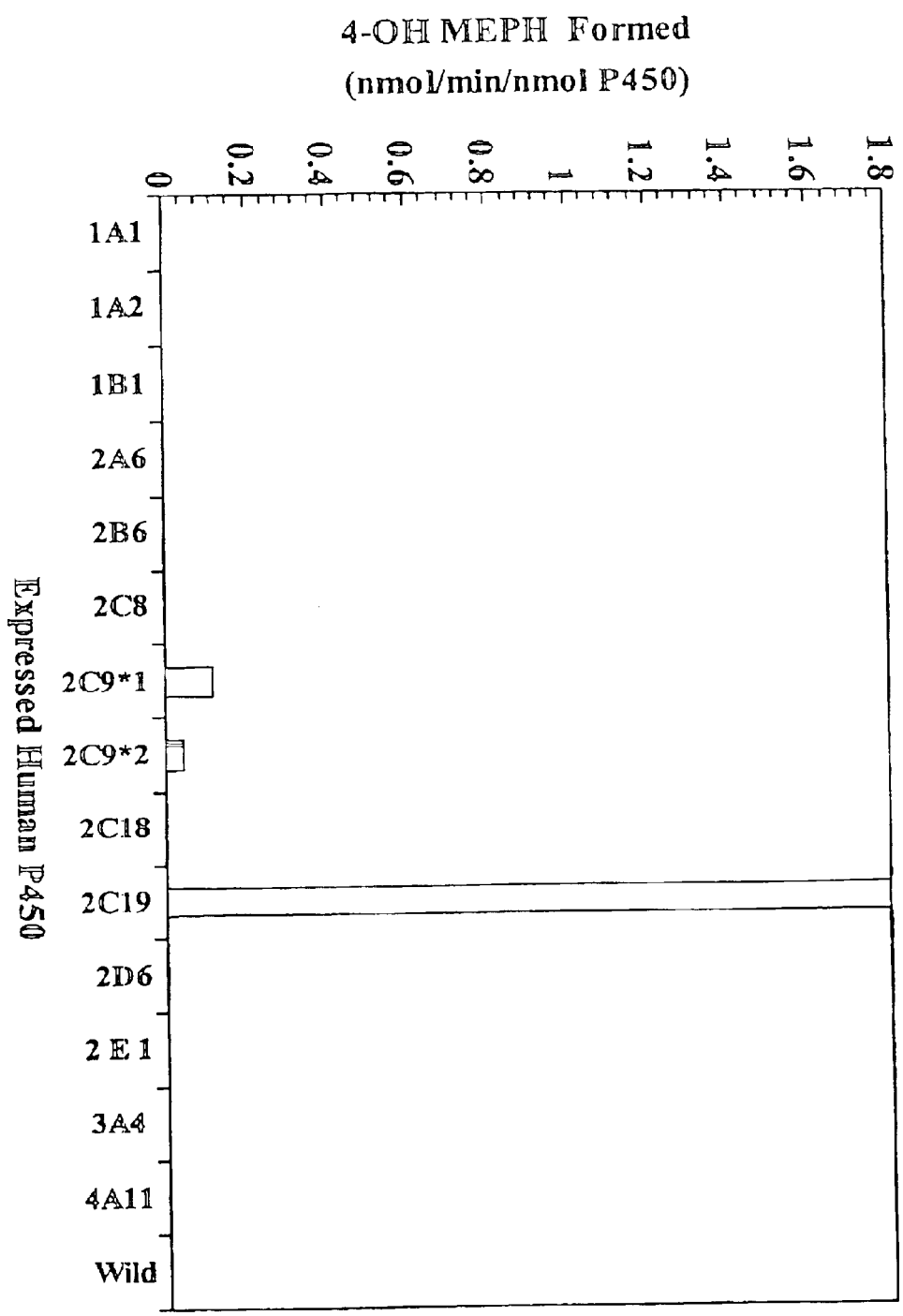
FIG. 2. Activity of human P450 cytochromes for the metabolic conversion of S-mephenytoin to its 4, hydroxy metabolite.

FIG. 2 shows the activity of fourteen expressed human P450s for the metabolic conversion of S-mephenytoin to its 4-hydroxy metabolite. S-mephenytoin has been used as a model substrate for the in vivo phenotyping of 2C 19 (Streetman et al., 2000). S-mephenytoin (100 $\mu$M) was incubated with 30–50 pmol of c-DNA expressed P450 in 1 mL of phosphate buffer containing 1 mM NADPH. The reaction was incubated for 1 hr. at 37° C. 4'-Hydroxymephenytoin was assay by HPLC as described in Materials and Methods. Data are the mean of duplicate incubations.

Figure 3:
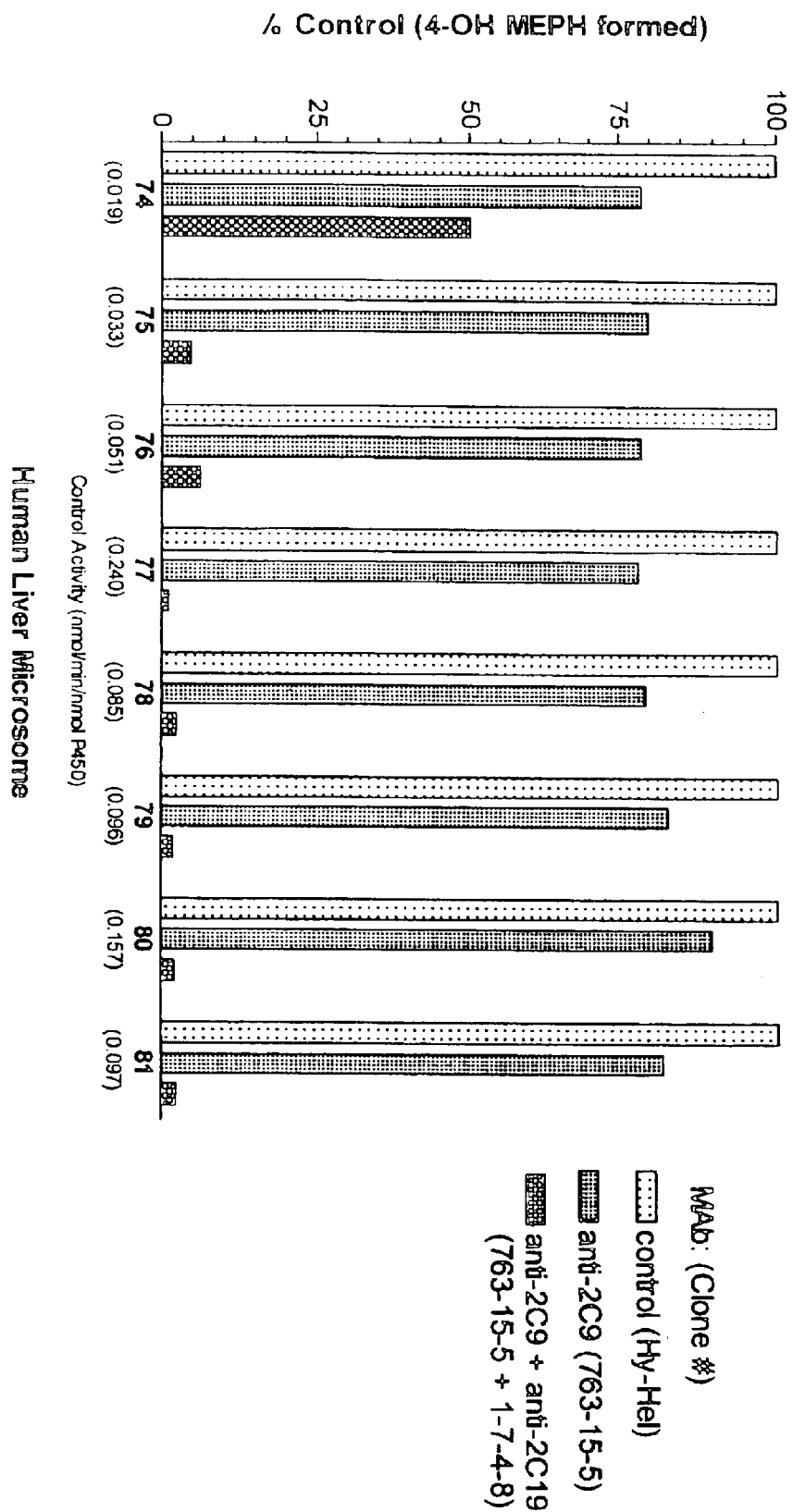
FIG. 3. Monoclonal antibody combinatorial analysis of S-Mephenytoin metabolism in human liver microsomes (HLM).

FIG. 3 shows MAb combinatorial analysis of S-mephenytoin metabolism in human liver microsomes. MAb 1-7-4-8 was an exemplary MAb utilized in this study. FIG. 3 shows also that 2C19 is the dominant enzyme metabolizing mephenytoin in HLM contributing about 80% of its metabolism. MAbs were added as indicated to 300 pmol of P450 in human liver microsomes (HLM) and pre-incubated for 5 min. at 37° C. The reaction was initiated by addition of S-mephenytoin (100 $\mu$M) and NADPH (1 mM) and allowed to proceed for 60 min. The metabolite was assayed by HPLC as described in material and methods. Hy-Hel, a MAb to lysozyme, was used as a control. Each bar represents the inhibition observed by the addition of the MAb(s) indicated and is relative to the bar preceding it. The 2C19 was the predominant expressed isoform exhibiting hydroxylase activity which was fifteen fold greater than the activity of 2C9* 1. The combinatorial addition of anti-2C9 and anti 2C19 showed, in contrast to the relative activities of the expressed enzymes, that 2C9 had a significant role in mephenytoin metabolism, contributing about 10–20% of activity in the eight HLM. The indication that 2C9 exhibits a role for mephenytoin metabolism suggests that mephenytoin metabolism is not an absolute measure for in vivo 2C19 phenotyping.

REFERENCES

Alvares A V, Schilling G, Garbut A and Kuntzman R (1970) Studies on the Hydroxylation of 3,4-benzpyrene by Hepatic Microsomes: Effect of Albumin on the Rate of Hydroxylation of 3,4-benzpyrene. *Biochem Pharmacol* 19:1449–1455.

Battula N, Sagara J and Gelboin H V (1987) Expression of P1-450 and P3-450 DNA Coding Sequences as Enzymatically Active Cytochromes P-450 in Mammalian Cells. *Proc Natl Acad Sci USA* 84:4073–4077.

Crespi C L (1995) Xenobiotic Metabolizing Human Cells as Tools for Pharmacological and Toxicological Research. *Adv in Drug Research* 26:180–216.

Crespi C L and Penman B W (1997) Use of cDNA Expressed Human Cytochrome P450 Enzymes to Study Potential Drug-Drug Interactions. *Adv in Pharmacology* 43:171–188.

Doillard T Y and Hoffman T (1983) Enzyme-linked Immunosorbant Assay for Screening Monoclonal Antibody. *Methods Enzymol* 92:168–174.

Edwards R J, Adams D A, Watts P A, Davies D S and Boobis A R (1998) Development of a Comprehensive Panel of Antibodies Against the Major Xenobiotic Metabolizing Forms of Cytochrome P450 in Humans. *Gene Expression and Development* 56(3):377–387.

Fujino T, Park S S, West D and Gelboin H V (1982) Phenotyping of Cytochromes P-450 in Human Tissues with Monoclonal Antibodies. *Proc Natl Acad Sci USA* 79:3682–3686.

Gelboin H V (1993) Monoclonal Antibodies and Cytochrome P450. *Pharmacol Rev* 45:413–453.

Gelboin H V, Krausz K W, Goldfarb I, Buters J T M, Yang S K, Gonzalez F J, Korzekwa K R and Shou M (1995) Inhibitory and Non Inhibitory Monoclonal Antibodies to Human Cytochrome P450 3A3/4. *Biochem Pharmacol* 50:1841–1850.

Gelboin H V, Goldfarb I, Krausz K W, Grogan J, Korzekwa K R, Gonzalez F J and Shou M (1996) Inhibitory and Noninhibitory Monoclonal Antibodies to Human Cytochrome P450 2E1. *Chem Res Toxicl* 9:1023–1030.

Gelboin H V, Krausz K W, Shou M, Gonzalez F J and Yang T J (1997) A Monoclonal Antibody Inhibitory to Human P450 2D6: A Paradigm for use in Combinatorial Determination of Individual P450 role in Specific Drug Tissue Metabolism. *Pharmacogenetics* 7:469–477.

Gelboin H V, Shou M, Goldfarb I, Yang T J and Krausz K W (1998) Monoclonal Antibodies to Cytochrome P450 in METHODS IN MOLECULAR BIOLOGY: CYTOCHROME P450 PROTOCOLS. (I R Phillips and E A Shephard, eds) pp 227–237, Humana Press Inc., Totowa, N.J.

Gelboin H V, Krausz K W, Gonzalez F J, and Yang T J (1999) Inhibitory Monoclonal Antibodies to Human Cytochrome P450 Enzymes: A New Avenue for Drug Discovery. *Trends Pharmacol Sci* 20(11):432–438.

Gonzalez F J and Korzekwa K R (1995) Human Cytochrome P450 Expression Systems. *Annu Rev Pharmacol Toxicol* 35:361–390.

Grogan J, Shou M, Andrusiak E A, Tamura S, Buters J T, Gonzalez F J and Korzekwa K R (1995) Cytochrome P450 2A1, 2E1, and 2C9 cDNA Expression by Insect Cells and Partial Purification using Hydrophobic Chromatography. *Biochem Pharmacol.* 50:1509–1515.

Harlow E and Lane D (1988) ANTIBODIES, A LABORATORY MANUAL. Cold Spring Harbor, N.Y.

Heyn H, White R B and Stevens S C (1996) Catalytic Role of Cytochrome P450 2B6 I the N-demethylation of S-mephenytoin. *Drug Metab and Dispos* 24:948–954.

Ioannides C (1996) CYTOCHROMES P450 METABOLIC AND TOXICOLOGICAL ASPECTS. CRC Press, New York.

Kimura S, Pastewka J V, Gelboin H V and Gonzalez F G (1987) cDNA and Amino Acid Sequences of Two Members of the Human P450II Gene Family. *Nucl Acids Res* 15:10053–10054.

Krausz K W, Goldfarb I, Yang T J, Gonzalez F J, and Gelboin H V (2000) An Inhibitory Monoclonal Antibody to Human Cytochrome P450 that Specifically Binds and Inhibits P450 2C9II, an Allelic Variant of P450 2C9 Having a Single Amino Acid Change Arg144 Cys. *Xenobiotica* 30:619–625.

Miners E D and Birkett D J (1998) Cytochrome P450 2C9: An Enzyme of Major Importance in Human Drug Metabolism. *Clin Pharmacol* 45:525–538.

Omura T. and Sato R (1964) The Carbon Monoxide-Binding Pigment of Liver Microsomes. Evidence for its Hemoprotein Nature. *J Biol Chem* 239:2370–2378.

Park S S, Waxman D J, Lapenson D P, Schenkman J B and Gelboin H V (1989) Monoclonal Antibodies to Rat Liver Cytochrome P-450 2c/RLM5 That Regiospecifically Inhibit Steroid Metabolism. *Biochem Pharmacol* 38(18):3067–3074.

Park, S S, Fujino, T, West, D, Guengerich, F P and Gelboin, H V (1982) Monoclonal Antibodies Inhibiting Enzyme Activity of Cytochrome P-450 from 3-Methycholanthracene-Treated Rats. *Cancer Res* 42:1798–1808.

Rahman A, Korzekwa K R, Grogan J, Gonzalez F J and Harris J W (1994) Selective Biotransformation of Taxol to 6α-hydroxytaxol by Human Cytochrome P450 2C8. *Cancer Res* 54:5543–5546.

Relling M V, Aoyama T, Gonzalez F J and Meyer U A (1990) Tolbutamide and Mephenytoin Hydroxylation by Human Cytochrome P450s in the 2C Subfamily. *J Pharmacol Exp Ther* 252:442–447.

Remmel R P and Burchell B (1995) Validation and Use of Cloned Expressed Human Drug Metabolizing Enzymes in Heterogeneous Cells for Analysis of Drug-Drug Interaction. *Biochem Pharmacol* 46:559–566.

Rendic S and DiCarlo F J (1997) Human Cytochrome P450 Enzymes: A Status Report Summarizing Their Reactions Substrates, Inducers and Inhibitors. *Drug Metab Rev* 29:413–580

Sai Y, Yang T J, Krausz K W, Gonzalez F J and Gelboin H V (1999) An Inhibitory Monoclonal Antibody to Human Cytochrome P450 2A6 Defines its Role in the Metabolism of coumarin, 7-ethoxycoumarin and 4-nitroanisole in Human Liver. *Pharmacogenetics* 9:229–237.

Schulz-Utermoehl T, Mountfield R J, Madsen K, Jorgensen P N, and Hansen K T (2000) Selective and Potent Inhibition of Human CYP2C19 Activity by a Conformationally Targeted Antipeptide Antibody. *Drug Metab and Dispos* 28:715–717.

Shimada T, Yamazaki H, Mimura M, Innui Y, Guengrich F P (1994) Interindividual Variations in Human Liver Cytochrome P450 Enzymes Involved in the Oxidation of Drugs, Carcinogens and Toxic Chemicals: Studies with Liver Microsomes of 30 Japanese and 30 Caucasions. *J Pharmacol Exp Ther* 270:414–423.

Streetman D S, Bertino J S, and Nafziger A N (2000) Phenotyping of Drug-Metabolizing Enzymes in Adults: A Review of In Vivo Cytochrome P450 Phenotyping Probes. *Pharmacogenetics* 10:187–216.

Venkatakrishnan K, Von Moltke L L, Court M H, Harmatz J S, Crespi C L and Greenblatt D J (2000) Comparison Between Cytochrome P450 (CYP) Content and Relative Activity Approaches to Scaling from cDNA Expressed CYPs to Human Liver Microsomes: Ratio of Accessory Proteins as Sources of Discrepancies Between the Approaches. *Drug Metab and Dispos* 28(12):1493–1504.

Wang R W and Lu A Y (1997) Inhibitory Anti-Peptide Antibody Against Human CYP3A4. *Drug Metab Dispos* 25:762–767.

Wester M R, Lasker J M, Johnson E F and Raucy J L (2000) CYP 2C19 Participates in Tolbutamide Hydroxylation by Human Liver Microsomes. *Drug Metab Dispos* 28(3):354–359.

Yang T J, Sai Y, Krausz K W, Gonzalez F J and Gelboin H V (1998a) Inhibitory Monoclonal Antibodies to Human Cytochrome P450 1A2: Analysis of Phenacetin o-Deethylation in Human Liver. *Pharmacogenetics* 8:375–382.

Yang T J, Krausz K W, Shou M, Yang S K, Buters J T M, Gonzalez F J and Gelboin H V (1998b) Inhibitory Monoclonal Antibody to Human Cytochrome P450 2B6. *Biochem Pharmacol* 55:1633–1640.

Yang T J, Shou M, Korzekwa K R, Gonzalez F J, Gelboin H V and Yang S K (1998c) Role of cDNA Expressed Human Cytochromes P450 in the Metabolism of Diazepam. *Biochem Pharmacol* 55:889–896.

Yang T J, Krausz K W, Sai Y, Gonzalez F J and Gelboin H V (1999) Eight Inhibitory Monoclonal Antibodies Define the Role of Individual P450 s in Human Liver Microsomal Diazepam, 7-Ethoxycoumarin and Imipramine Metabolism. *Drug Metab Dispos* 27:102–109.

Yelton D E and Scharff M D (1981) Monoclonal Antibodies: A Powerful New Tool in Biology and Medicine. *Annu Rev Biochem* 50:657–680.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

What is claimed is:

1. An isolated antibody or fragment thereof that competes with a monoclonal antibody selected from the group consisting of MAb 1-7-4-8 (ATCC PTA-3970), MAb 1-5-1-3 (ATCC PTA-3969), and MAb 1-1-11-1 (ATCC PTA-3971) for specific binding to human cytochrome P450 2C19, and that specifically inhibits 2C19-catalyzed metabolism of diazapam, mephenytoin and phenanthrene by at least 85%.

2. The isolated antibody or fragment thereof of claim 1 that is a monoclonal antibody.

3. The isolated antibody or fragment thereof of claim 1 that lacks specific binding to at least one cytochrome P450 selected from the group consisting of human cytochromes P450 1A1, 1A2, 1B1, 2A6, 2B6, 2C8, 2C9*1, 2C9*2, 2C9*3, 2C18, 2D6, 2E1, 3A4, and 3A5.

4. The isolated antibody or fragment thereof of claim 1 that lacks specific binding to each of human cytochromes P450 1A1, 1A2, 1B1, 2A6, 2B6, 2C8, 2C9*1, 2C9*2, 2C9*3, 2C18, 2D6, 2E1, 3A4, and 3A5.

5. The isolated antibody or fragment thereof of claim 1 that specifically inhibits the enzyme activity of human cytochrome P450 2C19 by at least 90%.

6. An isolated antibody or fragment thereof of claim 1 that is MAb 1-7-4-8 (ATCC PTA-3970) or a binding fragment thereof.

7. An isolated antibody or fragment thereof of claim 1 that is MAb 1-5-1-3 (ATCC PTA-3969) or a binding fragment thereof.

8. An isolated antibody or fragment thereof of claim 1 that is MAb 1-1-11-1 (ATCC PTA-3971) or a binding fragment thereof.

9. The monoclonal antibody of claim 2 that is a Fab fragment.

10. The monoclonal antibody of claim 2 that is a mouse antibody.

11. A cell line that produces the monoclonal antibody of claim 2.

12. The cell line of claim 11 that is an eucaryotic cell line.

13. The cell line of claim 11 that is a procaryotic cell line.

14. The monoclonal antibody of claim 2 comprising a light chain variable domain, wherein the light chain variable domain comprises three CDR regions from the light chain of a monoclonal antibody selected from the group, and the heavy chain variable domain comprises three CDR regions from the heavy chain of a monoclonal antibody selected from the group.

* * * * *